United States Patent [19]

Crooker et al.

[11] Patent Number: 5,177,270

[45] Date of Patent: * Jan. 5, 1993

[54] STABILIZED 141B

[75] Inventors: Richard M. Crooker, Lehigh; Maher Y. Elsheikh, Tredyffrin, both of Pa.

[73] Assignee: Elf Atochem North America, Inc., Philadelphia, Pa.

[*] Notice: The portion of the term of this patent subsequent to Dec. 8, 2009 has been disclaimed.

[21] Appl. No.: 773,485

[22] Filed: Oct. 9, 1991

[51] Int. Cl.⁵ .................. C07C 17/42; C07C 19/02

[52] U.S. Cl. .................. 570/119; 252/182.2; 252/182.24

[58] Field of Search .................. 570/119

[56] References Cited

FOREIGN PATENT DOCUMENTS 1-056632  3/1989  Japan .................. 570/119
1-265042 10/1989  Japan .................. 570/119

Primary Examiner—Joseph E. Evans

[57] ABSTRACT

Compositions of 141b which are stabilized with 4-benzyloxyphenol or 2,6-di-t-butyl-4-methylphenol.

4 Claims, No Drawings

STABILIZED 14LB

FIELD OF THE INVENTION

This invention relates to novel compositions containing 1,1-dichloro-1-fluoroethane ("141b") and stabilizing additives (or inhibitors) such as 2,6-di-t-butyl-4-methylphenol, more particularly to compositions of 141b which are stabilized against decomposition in polyol premix formulations or the corresponding polyurethane or polyisocyanurate foams made therefrom.

BACKGROUND OF THE INVENTION

Polyurethane and polyisocyanurate foams are conventionally prepared by reacting an organic polyisocyanate (including diisocyanate) "A-side" component with a "B-side" polyol premix component containing organic polyol, blowing agent, surfactant, catalyst, and possibly other additives such as flame retardants, antioxidants, and U.V. stabilizers. These A-side and B-side components may be purchased by the end-user in separate containers and stored for later use. Since decomposition of the 141b blowing agent has been observed in the B-side premixes during storage and during the process of making the foam, 141b compositions inhibited against such decompositions would be highly desirable. For example, 141b has been observed to decompose during the foam-making process to up to about 1%, depending on the formulation and reaction conditions, of various decomposition products of which by far the predominant product is 1-chloro-1-fluoroethylene ("1131a"). Inhibition of such decomposition is desired both because of toxicity concerns and because the decomposition is accompanied by the formation of equivalent amounts of acid which in turn causes catalyst deactivation.

SUMMARY OF THE INVENTION

A composition is provided containing the blowing agent 141b and an inhibitor selected from 4-benzyloxyphenol or, preferably, 2,6-di-t-butyl-4-methylphenol. When incorporated in a premix, the composition may also contain a polyol and, optionally, other ingredients such as surfactants, catalysts, and flame retardants.

DETAILED DESCRIPTION OF THE INVENTION

It has now been found that 141b is stabilized against decomposition by the addition of an inhibitor selected from 4-benzyloxyphenol or 2,6-di-t-butyl-4-methylphenol.

The inhibitor is present in an effective amount, typically from about 0.01 to about 2% by weight, based on the weight of 141b, preferably 0.05 to 1%.

The compositions may also include a polyol or a fully formulated B-side formulation containing polyol, catalyst, surfactant, and, optionally, other additives. Typical polyols are, for example, Stepanol PS 2502A, an aromatic polyester polyol sold by the Stepan Company; Terate 203, an aromatic polyester polyol sold by Hercules, Inc.; Pluracol Polyol 975, a sucrose-based polyol sold by BASF; Poly-G 71-530, a polyether polyol sold by Olin; and Quadrol, an amine-based polyol supplied by BASF. Typical catalysts include Potassium HEX-CEM, a potassium octoate sold by Mooney Chemicals; Polycat 41, an N,N,N-tri(dimethylaminopropyl)cyclohexatriazine catalyst sold by Air Products; Polycat 8, an N,N-dimethylcyclohexylamine catalyst sold by Air Products; Dabco TMR-30, a 2,4,6-tri(dimethylaminomethyl)phenol supplied by Air Products; and Dabco K-15, a potassium 2-ethylhexoate in diethylene glycol supplied by Air Products. A typical surfactant is Dow Corning 193, a silicone polymer surfactant. A typical A-side component is Mondur E-489, an aromatic diisocyanate supplied by Mobay Chemical Co., or Lupranate M20S, a polymethylenediisocyanate supplied by BASF.

The invention was illustrated by first preparing a polyurethane foam with 141b in the absence of inhibitor by stirring a formulation containing polyol (100g of Stepanol PS 2502A), 141b (25.8g), surfactant (1.51g of Dow Corning 193), catalyst (2.82g of Potassium HEXCEM and 0.7g of Polycat 41), and diisocyanate (127.2g of Mondur E-489). The contents were poured into a box and the resulting foam was left to cool to room temperature. After curing the foam at 250° F. for 20 hours, the cell gas was analyzed by crushing a sample and injecting the released gas mixture directly to a gas chromatograph. The gas was found to contain 2180 ppm of 1131a, whereas the 141b starting material contained only 10 ppm of 1131a. Other minor components in the cell gas totalled only about 440 ppm, similar to the levels found in the 141b starting material. When 0.6 weight % of each of 4-benzyloxyphenol and 2,6-di-t-butyl-4-methylphenol were dissolved in 141b, foams prepared as aforesaid contained only 1363 ppm and 1153 ppm of 1131a, respectively.

What is claimed is:

1. A composition stable against the formation of 1-chloro-1-fluoroethylene during its use as a foam blowing agent comprising 1,1-dichloro-1-fluoroethane and an inhibitor which consists of a phenol selected from 4-benzyloxyphenol and 2,6-di-t-butyl-4-methylphenol.

2. A composition as in claim 1 wherein the inhibitor is 2,6-di-t-butyl-4-methylphenol.

3. A method of stabilizing 1,1-dichloro-1-fluoroethane against the formation of 1-chloro-1-fluoroethylene during its use as a foam blowing agent which comprises the addition thereto of an effective amount of an inhibitor consisting of a phenol selected from 4-benzyloxyphenol and 2,6-di-t-butyl-4-methylphenol.

4. A method as in claim 3 wherein the phenol is 2,6-di-t-butyl-4-methylphenol.

* * * * *